(12) United States Patent
Elbers et al.

(10) Patent No.: US 6,703,231 B2
(45) Date of Patent: Mar. 9, 2004

(54) GM-NEGATIVE EHV-MUTANTS

(75) Inventors: Knut Elbers, Gau-Algesheim (DE); Nikolaus Osterrieder, Wampen (DE); Christian Seyboldt, Hannover (DE)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 0 days.

(21) Appl. No.: 09/789,495

(22) Filed: Feb. 16, 2001

(65) Prior Publication Data

US 2003/0198650 A1 Oct. 23, 2003

(30) Foreign Application Priority Data

Feb. 17, 2000 (EP) .......................................... 00 103 241

(51) Int. Cl.[7] .............................. C12N 7/00; C12N 7/01

(52) U.S. Cl. ............................... 435/235.1; 424/184.1; 424/204.1; 424/229.1; 435/5; 435/6; 435/7.1; 530/300; 530/350

(58) Field of Search ........................... 424/184.1, 204.1, 424/229.1; 435/5, 6, 7.1, 235.1; 530/300, 350

(56) References Cited

U.S. PATENT DOCUMENTS 5,922,327 A * 7/1999 Crabb et al. ............. 424/229.1

OTHER PUBLICATIONS

Neubauer et al. 1997 Virology 239: 36–45.*

Newubauer, A. et al: “Equine herpesvirus 1 mutants devoid of glycorprotein B or M are apathogenic for mice but induce protection against challenge infection.”; Virology (Dec. 1997), 239(1):36–45.

Osterrieder, N. et al: “The Equine Herpesvirus 1 Glycorprotein gp21/22a, the Herpes Simplex Virus Type 1 gM Homolog, is involved in Virus Penetration and Cell–to–Cell Spread of Virions”; J. of Virol., 70(6):4110–4115.

Seyboldt, C. et al: “Equine herpesvirus 1 (EHV–1) glycoprotein M: Effect of deletions of transmembrane domains”; Virology, (Dec. 2000) 278(2):477–489.

* cited by examiner

*Primary Examiner*—Jeffrey Stucker
*Assistant Examiner*—Myron G. Hill
(74) *Attorney, Agent, or Firm*—Robert P. Raymond; Susan K. Pocchiari; Mary-Ellen M. Devlin

(57) ABSTRACT

This invention relates to Equine Herpes Viruses (EHV) wherein the protein gM is essentially absent or modified and non-functional with respect to its immunomodulatory capacity. Further aspects of the invention relate to nucleic acids coding said viruses, pharmaceutical compositions comprising these viruses or nucleic acids and uses thereof. The invention also relates to methods for improving the immune response induced by an EHV vaccine against wild type EHV infections, methods for the prophylaxis and treatment of EHV infections and methods for distinguishing wild type EHV infected animals from animals treated with EHV's according to the invention.

17 Claims, 4 Drawing Sheets

Figure 4: *Bam*HI restriction map and genomic organization of the gM region of EHV-1 strain RacH-Virus and structure of gM-negative RacH virus HΔgM3b1. Restriction enzyme sites used for cloning are given, as are the scales.

GM-NEGATIVE EHV-MUTANTS

FIELD OF THE INVENTION

The present invention relates to Equine Herpes Viruses (EHV) wherein the protein gM is essentially absent or wherein gM is modified and non-functional with respect to its immunomodulatory capacity. Further aspects of the invention relate to nucleic acids coding said viruses, pharmaceutical compositions comprising these viruses or nucleic acids and uses thereof. The invention also relates to methods for improving the immune response induced by an EHV vaccine against wild type EHV infections, methods for the prophylaxis and treatment of EHV infections and methods for distinguishing wild type EHV infected animals from animals treated with EHV's according to the invention.

BACKGROUND OF THE INVENTION

Equine herpesvirus 1 (EHV-1), a member of the Alphaherpesvirinae, is the major cause of virus-induced abortion in equids and causes respiratory and neurological disease. The entire DNA sequence of the EHV-1 strain Ab4p has been determined (Telford, E. A. R. et al., 1992, Virology 189:304–316); however, only few genes and gene products have been characterized for their relevance for the virulence of EHV. For control of EHV-1 infections, two different approaches are followed. First, modified live vaccines (MLVs) have been developed, including the strain RacH (Mayr, A. et al., 1968, J. Vet. Med. B 15:406–418; Hübert, P. H. et al., 1996, J. Vet. Med. B 43:1–14), which is widely used in Europe and the United States. Second, inactivated vaccines and independently expressed viral glycoproteins have been assessed for their immunogenic and protective potential. Among the glycoproteins that were expressed using recombinant baculoviruses are the glycoproteins (g) B, C, D, and H, which induced partial protection against subsequent challenge EHV-1 infection in a murine model (Awan, A. R. et al., 1990, J. Gen. Virol. 71:1131–1140; Tewari, D. et al., 1994, J. Gen. Virol. 75:1735–1741; Osterrieder, N. et al., 1995, Virology 208:500–510; Stokes, A. et al., 1996, Virus Res. 40:91–107). However, the use of MLVs has advantages over killed and subunit vaccines. MLVs are highly efficient in inducing cell-mediated immune responses, which are most likely to be responsible for protection against disease (Allen, G. P. et al., 1995, J. Virol. 69:606–612; Mumford, J. A. et al., 1995, Proceedings 7$^{th}$ International Conference of Equine Infectious Disease (H. Nakajima and W. Plowright, Eds. 261–175 R & W Publ., Newmarket, U.K. United Kingdom).

Herpesvirus glycoproteins are crucially involved in the early stages of infection, in the release of virions from cells, and in the direct cell-to-cell spread of virions by fusion of neighboring cells. To date, 11 herpes simplex virus type 1 (HSV-1)-encoded glycoproteins have been identified and have been designated gB, gC, gD, gE, gG, gH, gI, gJ, gK, gL, and gM. HSV-1 mutants lacking gC, gE, gG, gI, gJ, and gM are viable, indicating that these genes are dispensable for replication in cultured cells. Comparison of the HSV-1 and equine herpesvirus 1 nucleotide sequences revealed that all of the known HSV-1 glycoproteins are conserved in EHV-1. According to the current nomenclature, these glycoproteins are designated by the names of their HSV-1 homologs. It is known that EHV-1 gC, gE and gI are not essential for growth in cell culture, whereas gB and gD are essential for virus growth in cultured cells. The contributions of other EHV-1 glycoproteins to replication in cultured cells are not known (Flowers, C. C. et al., 1992, Virology 190:307–315). Six envelope glycoproteins of EHV-1 were mapped by using a λgt11 expression library and monoclonal antibodies (mAbs) raised against purified EHV-1 (Allen, G. P. et al, 1987, J. Virol. 61:2454–2461). In addition, transcriptional and protein analyses have shown that the glycoproteins gB, gC, gD, gG, gH, and gK are expressed in EHV-1-infected cells. Glycoprotein gM (encoded by gene UL10 [Baines, J. D. et al., 1991, J. Virol. 65:938–944; Baines, J. D. et al., 1993, J. Virol. 67:1441–1452]) is the most recent HSV-1 glycoprotein which has been analyzed in detail. It is the only reported nonessential glycoprotein which is conserved in all herpes viral subfamilies and has been described for human and murine cytomegalovirus and the Gammaherpesvirinae members EHV-2, herpesvirus saimiri, and Epstein-Barr virus. Like many herpesvirus glycoproteins, HSV-1 gM is present in virions and membranes of infected cells. HSV-1 mutants solely lacking gM grew to titers reduced approximately 10-fold relative to those of wild-type virus and showed a reduced virulence in a murine model (Baines, J. D. et al., 1991, J. Virol. 65:938–944; MacLean, C. A. et al., 1993, J. Gen. Virol. 74:975–983). The EHV-1 gM homolog (gp21/22a; referred to as EHV-1 gM from now on) was first described by Allen and Yeargan (Allen, G. P. et al, 1987, J. Virol. 61:2454–2461) and was shown to be a major constituent of the virus envelope. Further investigations revealed that gene 52, the gene homologous to HSV-1 UL10, encodes the 450-amino-acid EHV-1 gM polypeptide (Pilling, A. et al., 1994, J. Gen. Virol. 75:439–442; Telford, E. A. R. et al., 1992, Virology 189:304–316). EHV-1 gM represents a multiple hydrophobic protein which contains eight predicted transmembrane domains and has been reported to be present in infected cells and in purified virions as an $M_r$ 45,000 protein (Pilling, A. et al., 1994, J. Gen. Virol. 75:439–442; Telford, E. A. R. et al., 1992, Virology 189:304–316).

In 1996 Osterrieder et al. (Virology 208:500–510) concluded from experiments that compared penetration characteristics of a viral mutant (L11 ΔgM) bearing an *Escherichia coli* lac Z gene inserted into the EHV-1 strain RacL11 gM gene (open reading frame 52) with those characteristics of the parental EHV-1 RacL 11 that the EHV-1 gM plays important roles in the penetration of virus into the target cell and in spread of the virus from cell to cell. In 1997, Neubauer et al. (Virology, 239:36–45) demonstrated that the above described EHV-1 insertion mutant of gM is attenuated and elicits protective immunity as demonstrated by the evaluation of virus-neutralizing antibodies and EHV-1-specific T-cells in spleens of immunized mice.

The technical problem underlying this invention was to provide new modified equine herpes viruses that demonstrate significantly improved immunogenic properties when used for the prophylaxis and treatment of EHV infections.

SUMMARY OF THE INVENTION

The invention relates to Equine Herpes Viruses (EHV) wherein the protein gM is essentially absent or wherein gM is modified and non-functional with respect to its immunomodulatory capacity. The invention also relates to nucleic acids encoding said viruses, pharmaceutical compositions comprising these viruses or nucleic acids and uses thereof. The invention also relates to methods for improving the immune response induced by an EHV vaccine against wild type EHV infections, methods for the prophylaxis and treatment of EHV infections and methods for distinguishing wild type EHV infected animals from animals treated with EHV's according to the invention.

LEGENDS TO THE FIGURES

FIG. 1: Mean Bodyweight Analyses

Figure 1:
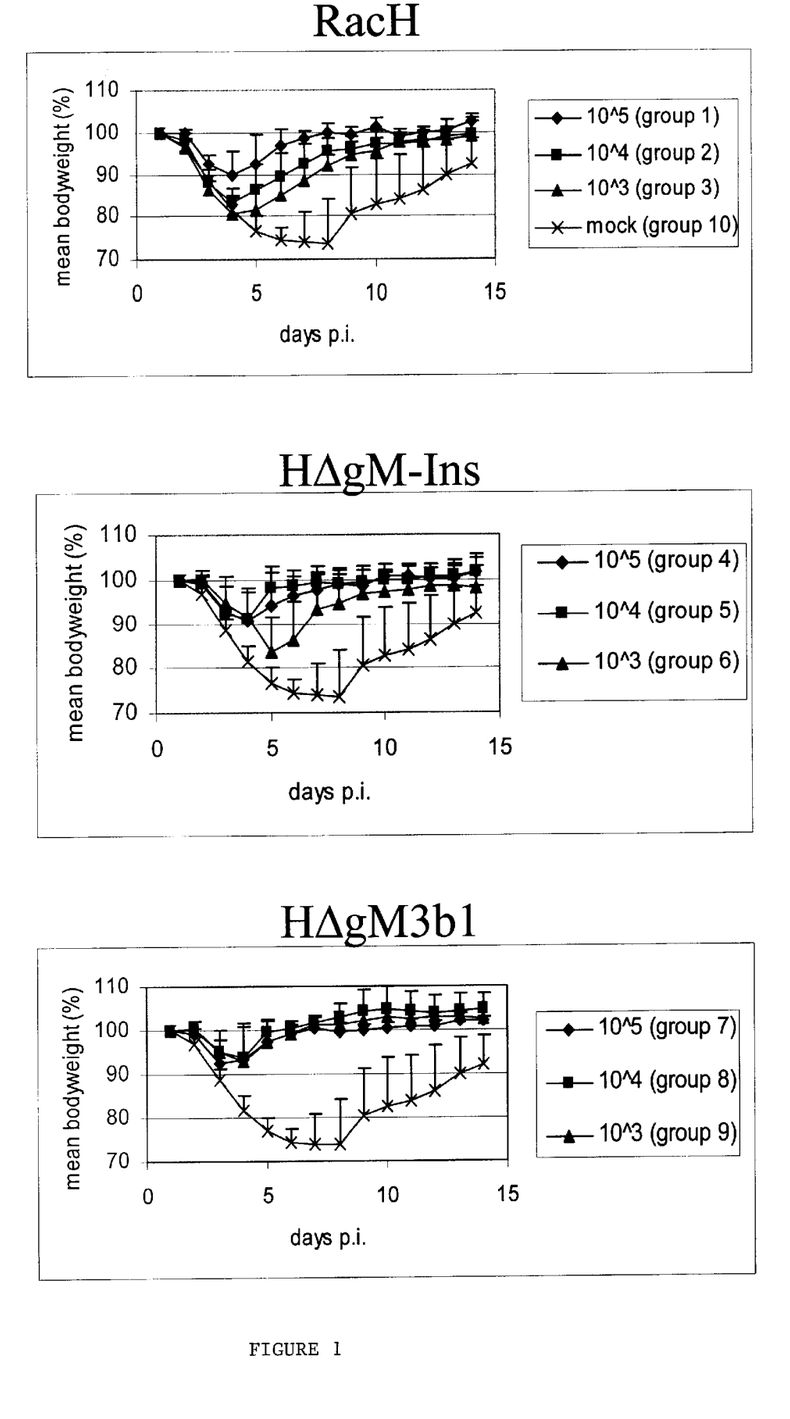
FIG. 1 shows the mean body weights given in percentage relative to the average body weight in the groups at day of challenge infection.

The HΔgM-3b1-immunized groups (groups 7 to 9) were compared to all other immunized groups to analyze a potential beneficial effect of this virus when compared to the other two viruses, because this virus exhibits an essentially complete deletion of glycoprotein M (AA 70-406 are deleted), whereas in case of HΔgM-Ins (groups 4 to 6) the gM open reading frame is interrupted by insertion of a LacZ cassette. However, this virus mutant still is capable of expressing the carboxy-terminal portion (probably starting at the methionine residue at pos. 226) of the gM open reading frame. RacH (groups 1 to 3) is the parental virus of both HΔgM-3b1 and HΔgM-Ins and represents a widely used vaccine strain.

Animals vaccinated with HΔgM-3b1 have the lowest transient body weight reduction in the those mice vaccinated with $10^3$ PFU (group 9) compared to groups vaccinated with $10^3$ PFU of HΔgM-Ins (group 6) or $10^3$ PFU of RacH (group 3). The dose dependency in the prevention of the weight reduction after challenge is lower in groups vaccinated with HΔgM-3b1 (groups 7–9), compared to groups vaccinated with HΔgM-Ins (group 4–6) or RacH (group 1–3).

Figure 2:
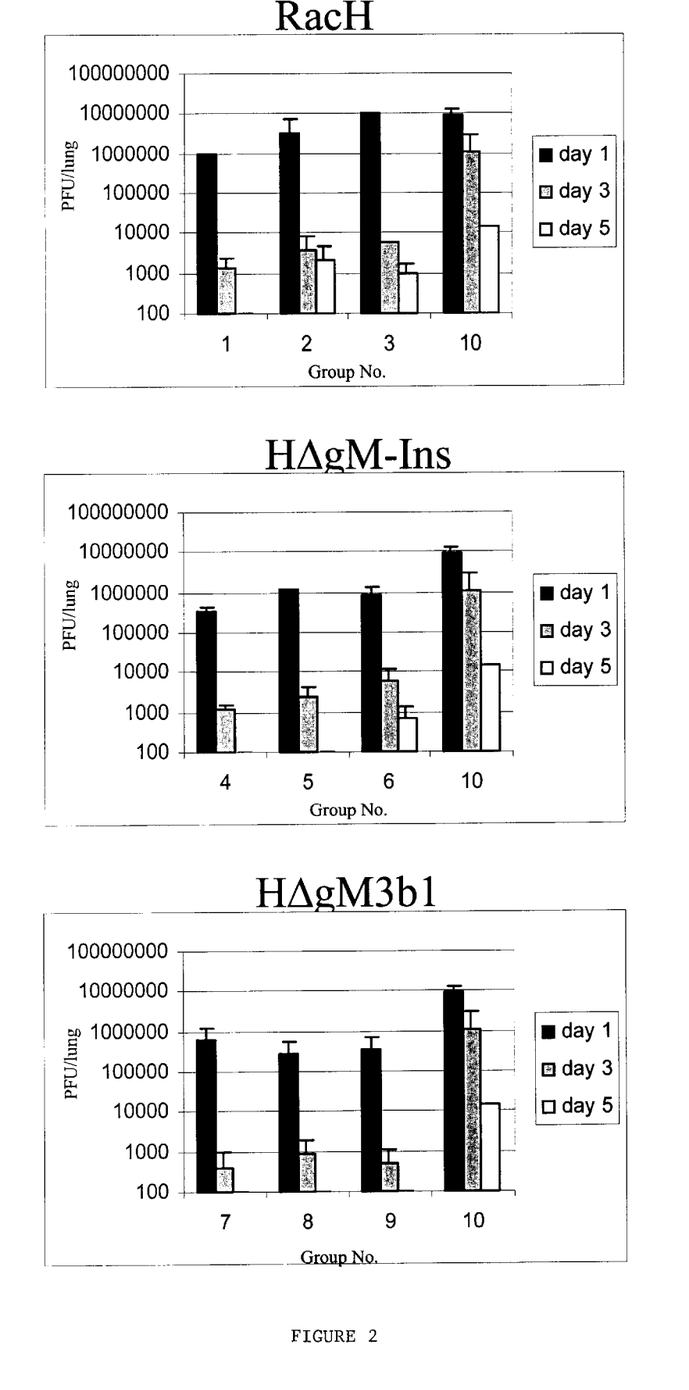
FIG. 2: Virus Titer Analysis

On Day 1 post infection (p.i.) 2 animals, on day 3 p.i. 3 animals, and on day 5 p.i. 2 animals per group were necropsied. Mouse lungs were prepared, homogenized with sea sand, and suspended in 1 ml of DMEM-10% FCS. Virus titer in the lung homogenate was determined by a plaque assay as described in Neubauer et al., 1997 (Virology 239:36–45). The data indicates that after immunisation with HΔgM-3b1 (groups 7 to 9) the amount of EHV virus reisolated from the lung tissue (each lung was prepared separately and the average of the virus titers obtained from the individual lungs is given in the figure) is reduced compared to HΔgM-Ins (groups 4 to 6) or RacH (groups 1–3) immunised mice. This effect is even stronger at the lowest vaccination dose ($10^3$ PFU) of the respective viruses, than with the higher doses ($10^4$ or $10^5$ PFU). Also the duration of viremia is shortened, as the amount of virus, which can be re-isolated from HΔgM-3b1 vaccinated animals after 5 days is markedly reduced compared to HΔgM-Ins or RacH vaccinated mice, especially in the groups vaccinated with the $10^3$ PFU dose.

Figure 3:
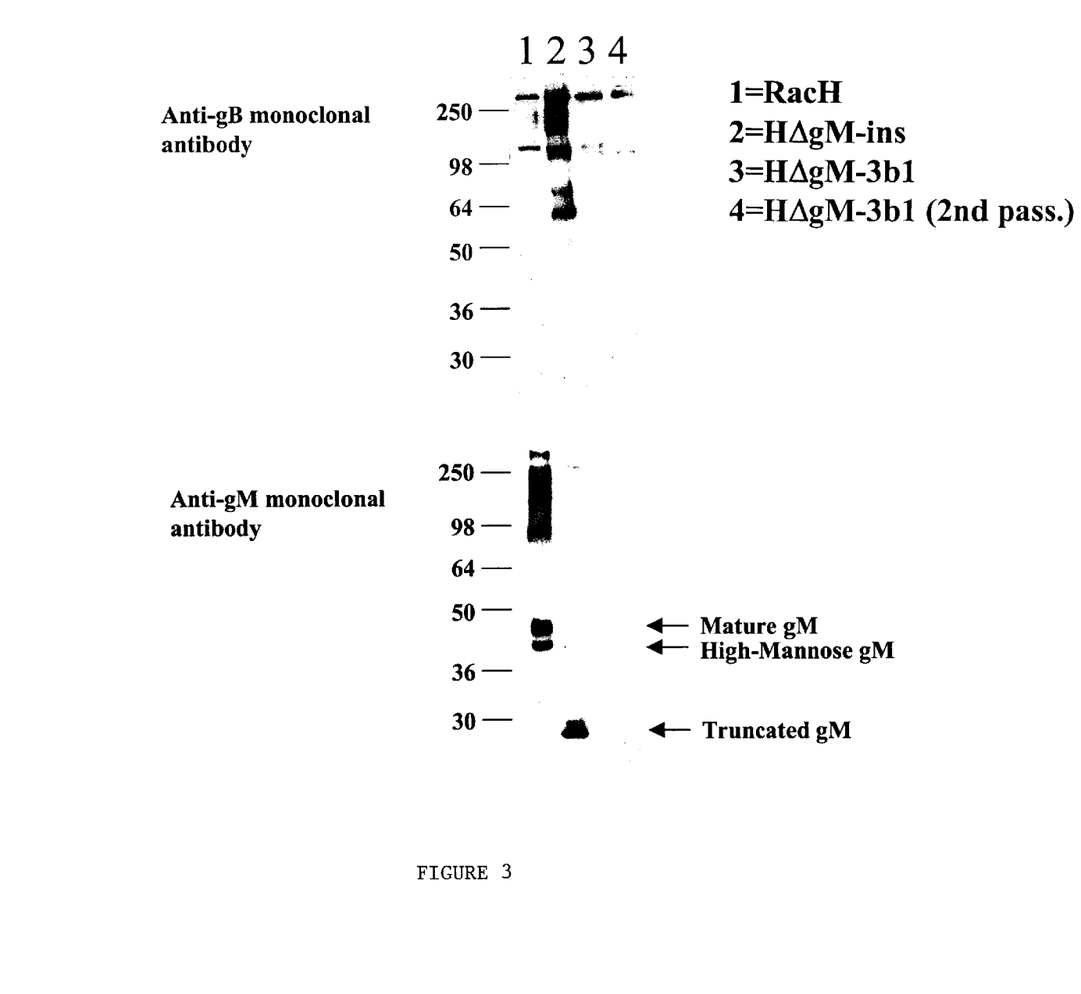
FIG. 3: Western Blot Analyses
Figure 4:
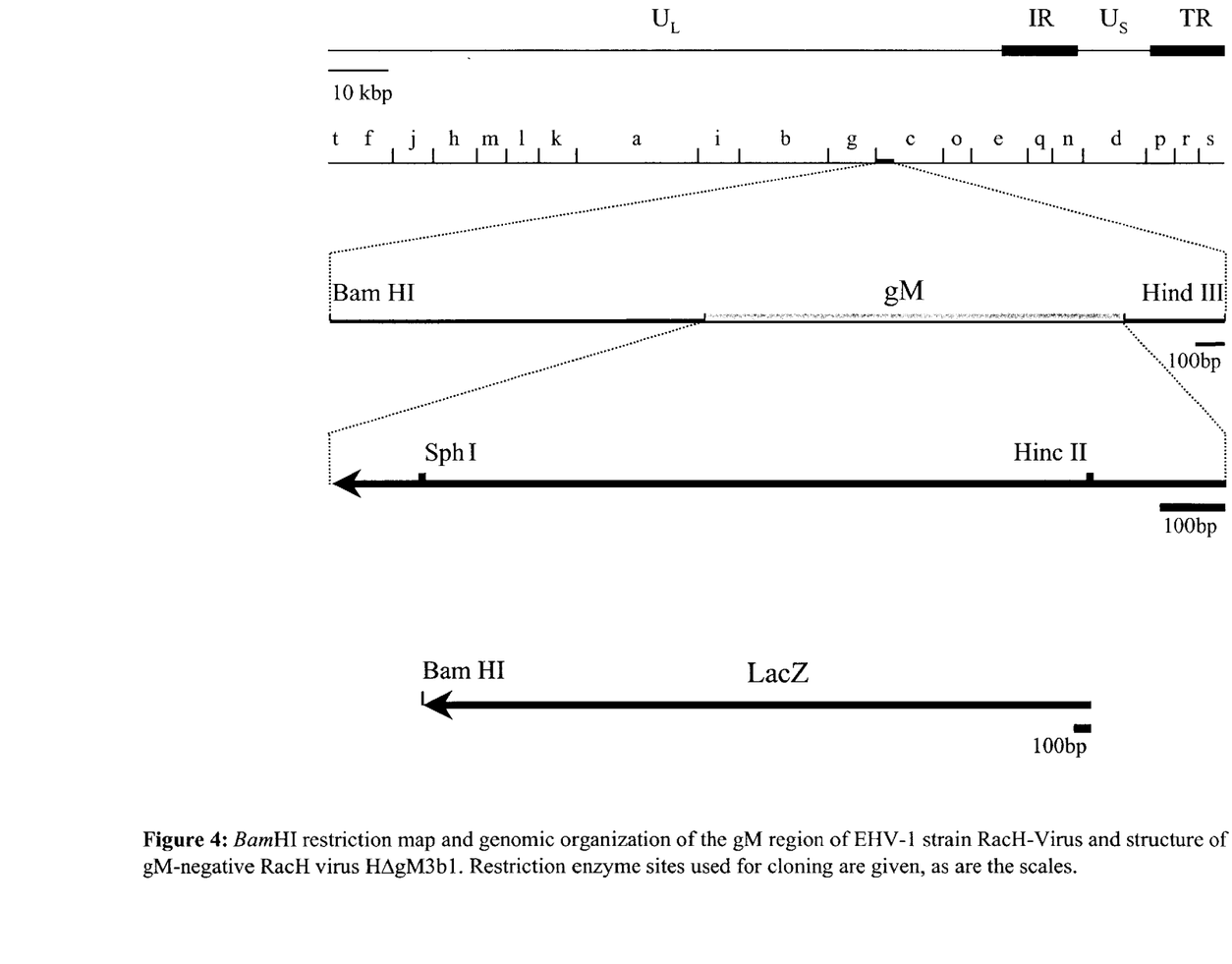

Western blot analysis of infected cell lysates using anti-gB mab 3F6 (Allen and Yeargan, 1987, J. Virol. 61:2454–2461; kindly provided by Dr. G. Allen, Lexington, Ky., U.S.A.) (A) or anti-gM mab A8 (kindly provided by Dr. R. A. Killington, Leeds, UK) (B). Cell lysates were suspended in sample buffer and immediately separated by SDS-10%-PAGE. Proteins were transferred to nitrocellulose sheets, incubated with the mabs, and detected as detailed in Materials and Methods. Lane 1: RacH infected cells; Lane 2: HΔgM-Ins (insertion mutant) infected cells; Lanes 3 HΔgM-3b1 infected cells; Lane 4 infected cells with the second passage of HΔgM-3b1 on Rk13 cells. In panel A, specific identification of gB in RacH, HΔgM-Ins and HΔgM-3b1 infected cells clearly indicates viral protein expression and virus replication in the infected cells. Di- and oligomers of gB are clearly visible indicating proper glycoprotein processing. In panel B, the monoclonal antibody A8 detected the gM protein with the expected apparent molecular weight in RacH-infected cells (lane 1). In the HΔgM-Ins, the open reading frame is interrupted by the inserted lacZ gene. Accordingly, the gM protein specifically identified has a lower apparent molecular weight (lane 2). As the intensity of the western blot signal of the gM protein expressed by HΔgM-Ins is comparable to the signal obtained in RacH infected cells, this clearly indicates that the truncation does not result in abrogation of gM protein expression or immediate degradation of the protein in the infected cells. Additionally, the carboxyterminal portion of gM appears to be expressed in the case of HΔgM-Ins because the A8 antibody is directed against the hydrophilic portion of the gM carboxyterminal end. In lanes 3 and 4, no gM protein can be detected as expected after deletion of the corresponding nucleotide sequences in HΔgM-3b1 as described above.

Material and Methods (Western Blot Analysis):

For Western blot analysis, infected-cell lysates were adjusted to equal protein concentrations using the BCA™ assay (Pierce), suspended in sample buffer (final concentration: 50 mM Tris-Cl, pH 6.8; 3.2% sodium dodecyl sulfate (SDS); 5% 2-mercaptoethanol; 10% glycerol). Samples were kept on ice throughout the procedure and not heated. Proteins were separated by discontinuous SDS-10% polyacrylamide gel electrophoresis (PAGE) (Laemmli, 1970, Nature 227:680–685), and transferred to nitrocellulose membranes (Schleicher & Schüll) by the semi-dry method (Kyhse-Andersen, 1984, J. Biochem. Biophys. Methods 10:203–210). After transfer, membranes were incubated in 10% skim milk in phosphate-buffered saline containing 0.05% Tween20 (PBS-T) for 16 hr at 4° C. Membranes were washed twice in PBS-T for 10 min at room temperature (RT) before anti-gB monoclonal antibody (mab) 3F6 (Allen and Yeargan, 1987, J. Virol 61:2454–2461) or anti-gM mab A8 (Day, L. 1999, PhD thesis, Department of Microbiology, University of Leeds, UK) were added at the indicated dilutions in PBS-T. Nitrocellulose sheets were incubated with the mabs for 1 hr at RT before two washes with PBS-T (10 min, RT) followed. Bound mabs were detected with peroxidase-conjugated anti-mouse immunoglobulin G antibodies (Sigma) for 1 hr at RT according to the supplier's instructions. After two final washing steps (PBS-T, 10 min), reactive bands were visualized by enhanced chemoluminescence (ECL™, Amersham-Pharmacia) according to the supplier's instructions.

FIG. 4: Schematic Description of the HΔgM-3b1 Genome

BamHI restriction map and genomic organization of the gM region of EHV-1 RacH virus and structure of gM negative RacH virus HΔgM-3b1. Restriction enzyme sites used for cloning are given, as well as scales.

DISCLOSURE OF THE INVENTION

The solution to the above technical problem is achieved by the description and the embodiments characterized in the claims.

It has surprisingly been found that there is a measurably improved protective immunity associated with equine herpes virus if the protein gM is essentially absent or said protein is modified and thereby rendered non-functional with respect to its presumed immunomodulatory capacity. Therefore, it has for the first time been demonstrated that the protein gM modulates the immunogenic properties of EHV. Interestingly, the previously discussed viral mutant L11ΔgM and HΔgM-Ins also elicits the immunogenic properties of the parental strain RacL11 and RacH. Although the authors of Osterrieder et al. 1996 and Neubauer et al. 1997

(Virology, 239:36–45) did not detect gM for HΔgM-Ins viruses with the available antibody at that time, the HΔgM-Ins mutant still demonstrates an immunomodulatory potential similar to the gM-producing parent strain. This is probably due to the remaining part of gM that is expressed in HΔgM-Ins despite the lacZ insert as demonstrated by Western blot analysis in the disclosed examples. This remaining portion of gM must therefore be responsible for the immunomodulatory action of gM. Consequently, the present invention provides for the first time EHV in which the protein gM is essentially absent or said protein is modified and non-functional with respect to its immunomodulatory capacity in the virus host.

In one aspect, the present invention relates to equine herpes virus wherein the protein gM is essentially absent.

In another equally important aspect the present invention relates to equine herpes virus wherein said protein is modified and non-functional.

The term "essentially absent" is used herein because of the position of the neighboring gene for the essential protein UL9 homolog (gene 53), its orientation and overlap with the gene coding for the protein gM, thus requiring that a minimal nucleotide sequence of the gene for gM must remain to allow the expression of gene 53 and thereby retain virus viability. One preferred embodiment refers to EHV wherein at least 70% of the gM gene is absent while in a more preferred embodiment an EHV is claimed wherein at least 80% of the gM gene is absent and in a most preferred embodiment an EHV is claimed wherein at least 90% of the gM gene absent.

The term "non-functional" protein gM is to be understood with respect to the protein's immunomodulatory impact with regard to the virus-host interaction. The difference between the immunogenic potential of an EHV according to the invention when compared to other EHV strains expressing functional gM can be determined by standard animal models available to the average expert in the state of the art of veterinary virology. One possible procedure for determining if an EHV expresses gM functionally or non-functionally is given in example 1. Said procedure provides one precise and straight forward experimental setup for determining the difference in the immunomodulatory capacity of a modified EHV strain of interest in comparison to strains that differ only in that they express a complete and unmodified functional protein gM. The procedure described in example 1 is especially suited since the behavior of EHV strains in BALB/c mice correlates with that of individual viruses in the natural host (Mayr, A. et al., 1968, J. Vet. Med. B 15:406–418; vanWoensel, P. A. et al., 1995, J. Virol. methods 54(1):39–49; Colle, C. F. et al., 1996, Vet. Microbiol. 48 (3–4):353–365; Hübert, P. H. et al., 1996, J. Vet Med. B 43:1–14; Matsumura, T. et al., 1996, Virus. Res. 43(2) 111–124).

For deleting the protein gM from an EHV or rendering it non-functional, various approaches are feasible (Sambrook, J. et al. 1989, Molecular Cloning: A laboratory manual. 2$^{nd}$ ed. Cold Spring Harbor Laboratory Press, Cold Spring Harbor, N.Y.). Non-limiting examples include the deletion, mutation, or insertion in the gene coding for the protein gM. Deletion of the corresponding complete or partial nucleotide sequence from said virus can result in the complete absence or non-functional expression of the gM protein. The same result can also be achieved by mutating the nucleotide sequence or inserting further nucleotides within the gene or in its regulatory region. In a preferred embodiment of both above-mentioned aspects, the invention relates to EHV according to the invention that are modified by a deletion, mutation, or insertion in the gene coding for the protein gM.

The gM ORF overlaps with the UL9 ORF and promoter sequences (position 94389 to 97052, Ori-binding protein, Telford et al. 1992, Virology 189:304–316). The protein coded by the UL9 ORF is essential for virus growth as shown in exemplary manner for HSV-1. (Carmichael et al. 1988, J. Virol. 62(1):91–99; Malik et al. 1992, Virology 190(2):702–715). Therefore, a more preferred embodiment the invention relates to EHV's according to the invention that are characterized in that the gene coding for the protein gM is deleted or modified and the expression of the gene coding for the UL9 homolog (gene 53) is not affected. The term "not affected" does not relate to a certain quantity or qualitative properties of UL9 but simply means that the expression of the gene is not affected as long as said protein is expressed by the virus and is present in an essentially sufficient amount for the viability of the virus.

The present invention discloses one most preferred EHV for practicing the invention wherein the nucleotides 93254 to 94264 as numbered for the virus strain EHV-1 Ab4p (Telford, E. A. R. et al. 1992, Virology 189:304–316) in an exemplary manner or corresponding thereto in other strains are deleted. The deletion of these 1010 nucleotides of the gM ORF of 1352 nucleotides altogether results in the essential absence of any detectable gM peptide. This almost complete deletion of the nucleotides of the gM gene still results in a viable virus that does essentially not express gM protein derivatives and whereby the expression of all other EHV-1 genes is not affected. This particular deletion does not affect the expression of the UL9 ORF.

The above-mentioned nucleotide positions are referenced for the EHV-1 strain Ab4p as numbered by Telford et al. 1992 (Virology 189:304–316) (GenBank/EMBL data library (accession number M86664). These nucleotide positions are by no means limited to the exact positions as defined for the Ab4p EHV-1 strain but are simply used in an exemplary manner to point out the nucleotides being at these positions or corresponding to those positions of the gM gene in other EHV strains. For different EHV viruses the numbering of the positions of the preferred nucleic acids might be different but an expert in the field of the molecular biology of viruses of the family Alphaherpesvirinae will easily identify these preferred nucleotides by their position relative to the other nucleotides of said sequences. It is important for the viability of the virus that the genes neighboring the gM gene are functionally expressed.

The most preferred EHV strain according to the invention is the EHV-1 strain HΔgM-3b1 designated Equine Herpes Virus Type 1 (RacHgM$^-$) and deposited under accession No. 99101536 with the ECACC (European Collection of Cell Cultures, Salisbury, UK).

The invention is particularly suitable for EHV of type 1 and 4 since both types are very closely related (Telford, E. A. R. et al., 1992, Virology 189:304–316 and 1998, J. Gen. Virol. 79:1197–1203).

The EHV of the present invention are particularly useful for gene therapy, for carrying heterologous material in general, and in particular for carrying foreign antigens for use in live vaccines (for EHV as heterologous vector, see EP 507179, WO 9827216, WO 9400587, WO 9827216). When an EHV of the invention expresses heterologous material in an animal there is no effect on the gM related immunological properties. EHV is especially suitable for immunising against other pathogens when antigens with immunologically relevant properties are expressed after insertion of the corresponding nucleotide sequences into the EHV genome of viruses according to the invention. Herpes virus vector vaccines are state of the art (see Schmitt, J. et al., 1999, J. Gen. Virol. 80:2839–2848, Peeters, B. et al., 1997, J. Gen. Virol. 78:3311–3315, Yokoyama et al., 1998, J. Vet. Med. Sci. 60:717–723). Therefore, in a preferred embodiment, the present invention also relates to EHV's according to the invention that carry one or more heterologous genes.

A further aspect of the invention relates to the nucleic acids coding for the EHV according to the invention. The nucleotides are useful for further modifying EHV or for the recombinant production of EHV's according to the invention. They are also useful for generating nucleic acid based vaccines.

Because of the improved immunological properties associated with EHV's, expressing a modified non-functional gM or not expressing gM at all, the EHV's of the invention are particularly suitable as active ingredients in a pharmaceutical composition for the prophylaxis and treatment of EHV infections. Therefore, in a further aspect, the invention relates to pharmaceutical compositions comprising an EHV according to the invention.

The nucleotides of the invention are also useful for preparing DNA vector-vaccines. In these vaccines, the nucleotides are applied directly to the animal or indirectly via vectors other than the original virus. Nucleotide vaccines and vector vaccines are well known from the present state of the art and will not be elaborated further.

In a further embodiment, the present invention relates to a pharmaceutical composition comprising a nucleic acid according to the invention. The invention also relates to pharmaceutical compositions comprising EHV's according to the invention.

One non-limiting example of a pharmaceutical composition comprising an EHV according to the invention, solely given for demonstration purposes, could be prepared as follows: Cell culture supernatant of an infected cell culture is mixed with a stabilizer (e.g. spermidine and/or BSA (bovine serum albumin)) and the mixture is subsequently lyophilized or dehydrated by other methods. Prior to vaccination, said mixture is then rehydrated in aqueous (e.g. saline, PBS (phosphate buffered saline)) or non-aqueous solutions (e.g. oil emulsion, aluminum-based adjuvant).

EHV and the nucleotides thereof are particularly well suited for their use for the preparation of a pharmaceutical composition.

A "pharmaceutical composition" essentially consists of one or more ingredients capable of modifying physiological e.g. immunological functions of the organism it is administered to or of organisms living in or on its surface like but not restricted to antibiotics or antiparasitics, as well as other constituents added to it in order to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

In another aspect the invention relates to a method for improving the immune response induced by an Equine Herpes Virus vaccine against wild type virus infections characterized in that the vaccine comprises an Equine Herpes Virus according to the invention.

A further aspect relates to a method for the prophylaxis and/or treatment of an animal characterized in that a pharmaceutical composition according to the invention is applied to said animal.

Another aspect of a modern live EHV vaccine is its ability to be distinguished from wild type viruses. The EHV's of the present invention differ at least in one important property from wild type isolates. They provide a significantly modified gM protein. Either gM is essentially absent or modified to an extent that this specific antigenic target differs sufficiently from the gM of wild type viruses.

One preferred embodiment relates to a method for distinguishing an animal infected with a wild type Equine Herpes Virus from an animal treated with a modified Equine Herpes Virus according to the invention, characterized in that the identity of a protein gM of the field virus or the identity of a protein gM as expressed or its essential absence in the modified virus is established.

A more preferred embodiment relates to the above-mentioned method, that is characterized in that a) a sample of interest is added to an isolated gM or modified derivatives thereof, b) an antibody specific for the isolated gM protein or modified derivatives thereof is added, c) the binding of said antibody is determined.

A most preferred embodiment relates to a method for distinguishing an animal infected with a wild type Equine Herpes Virus from an animal treated with a modified Equine Herpes Virus according to the invention, characterized in that the difference in the nucleic acids coding for the field virus protein gM and the nucleic acids coding for the modified gM protein or their absence is established.

A further aspect of the invention relates to kits for performing the preferred methods for distinguishing wild type EHV infected animals from animals treated with modified EHV's according to the invention. It is preferable to contain one or more of the necessary analytical tools, buffers, markers and readout tools, solvents and mechanical devices in one convenient kit. The preferred specific analytical tools are isolated wild type protein gM, isolated modified protein gM, antibodies specific for wild type protein gM, antibodies specific for the isolated modified protein gM, as well as nucleotide specific probes that bind to the nucleotides coding for the wild type protein gM and nucleotide specific probes that bind to the nucleotides coding for the modified protein gM.

EXAMPLES

Example 1

Test for gM Impact on Virus Immunogenic Properties

Experimental Design:

Three- to four-week old BALB/c mice (Charles River) were randomly divided into 10 groups consisting of 14 animals each and immunized intranasally (i.n.) with RacH (groups 1 to 3), the gM-negative insertion mutant HΔgM-Ins (Neubauer et al., 1997 Virology 239:36–45) (groups 4 to 6) or HΔgM3b1 virus lacking essentially the entire gM open reading frame (groups 7 to 9). Mice were immunised by a single application of $1 \times 10^5$ plaque-forming units (PFU) (groups 1, 4, 7), $1 \times 10^4$ PFU (groups 2, 5, 8), or $1 \times 10^3$ PFU (groups 3, 6, 9) in 20 µl as indicated. Mock-infection of mice (group 10) was done using 20 µl of DMEM-10% FCS. Twenty-nine days after immunization, mice were infected i.n. with $1 \times 10^5$ PFU of strain RacL11 suspended in 20 µl. Body weights of individual mice were scored daily from the day of infection (Day 0) to Day 13. Relative body weights (in %) were determined on Days 0 to 13 according to the equation: Weight Day n/Weight Day 0×100. On Day 1 post infection (p.i.) 2 animals, on day 3 p.i. 3 animals, and on day 5 p.i. 2 animals per group were necropsied. Mouse lungs were prepared, homogenized with sea sand, and suspended in 1 ml of DMEM-10% FCS (Meindl and Osterrieder, 1999, J. Virol 73(4):3430–7). Virus titers in murine lungs were determined on Rk13 cells (Neubauer et al., 1997, Virology 239:36–45). Statistical analyses of daily recorded body-weights were done as described below.

Objective of the Study:

The primary objective of this study was to demonstrate differences in the protective potential after immunization with HΔgM-3b1 (groups 7 to 9) when compared to RacH (groups 1 to 3) and HΔgM-Ins (groups 4 to 6) as determined by the parameter body weight after challenge infection with a virulent EHV-1 strain. The secondary objectives were to compare groups 1 to 9 with the mock-infected group -continued Average weight of mice in groups in gram
in italics the standard deviations in the groups are given

| | Group No. | | | | | | | | | |
|---|---|---|---|---|---|---|---|---|---|---|
| DPI* | 6 | | 7 | | 8 | | 9 | | 10 | |
| 8  | 17,00 | *1,6817* | 18,10 | *1,1331* | 16,93 | *2,8099* | 17,19 | *1,1922* | 12,66 | *1,9100* |
| 9  | 17,38 | *1,4892* | 18,18 | *1,0759* | 17,01 | *2,5142* | 17,31 | *1,0699* | 13,80 | *2,0347* |
| 10 | 17,52 | *1,6130* | 18,27 | *1,0893* | 17,07 | *2,4635* | 17,51 | *1,0885* | 14,15 | *2,1142* |
| 11 | 17,55 | *1,5333* | 18,32 | *1,1179* | 17,11 | *2,1721* | 17,44 | *1,0706* | 14,40 | *1,9849* |
| 12 | 17,77 | *1,5410* | 18,28 | *1,0962* | 17,24 | *2,2693* | 17,49 | *1,0007* | 14,78 | *1,8945* |
| 13 | 17,72 | *1,5211* | 18,55 | *1,0095* | 17,37 | *2,4432* | 17,47 | *1,0128* | 15,40 | *1,5033* |
| 14 | 17,68 | *1,4959* | 18,53 | *1,0093* | 17,43 | *2,3915* | 17,43 | *1,1086* | 15,83 | *1,1615* |

*DPI = Days Post Infection

1. Comparison of mock-infected animals (Group 10) with immunized animals The following table demonstrates that mean body weights of mock-immunized animals were statistically significantly (day 3) or highly statistically significantly (days 4 to 13) reduced after challenge infection when compared to all other groups.

TABLE 1

| Group 10 vs Others | F-Value[1] | p-Value |
|---|---|---|
| Day 1[2] | 2.56 | 0.1156 |
| Day 2 | 1.33 | 0.2541 |
| Day 3 | 9.03 | 0.0040* |
| Day 4 | 20.46 | 0.0001** |
| Day 5 | 54.83 | 0.0001** |
| Day 6 | 72.31 | 0.0001** |
| Day 7 | 84.82 | 0.0001** |
| Day 8 | 61.62 | 0.0001** |
| Day 9 | 52.91 | 0.0001** |
| Day 10 | 40.47 | 0.0001** |
| Day 11 | 35.21 | 0.0001** |
| Day 12 | 24.18 | 0.0001** |
| Day 13 | 18.52 | 0.0001** |

[1]test statistic
[2]Statistics are given from DAY 1 to 13; At DAY 0, all calculations are identical (weights set to 100%)
*statistically significant (<0.05)
**highly statistically significant (<0.0001)

2. Comparison of HΔgM-3b1-immunized animals (group 7, $10^5$ PFU/animal) with RacH-(group 1, $10^5$ PFU) and HΔgM-Ins-immunized animals (group 4, $10^5$ PFU) regarding the efficacy parameter prevention of body weight reduction after challenge infection.

The results given in the following table demonstrate that no statistically significant differences in mean body weights could be observed in groups immunized with the highest dose of virus, irrespective of the agent used for immunization.

TABLE 2

| | F-Value[1] | p-Value |
|---|---|---|
| Group 7 vs Group 4 | | |
| Day 1[2] | 0.00 | 0.9452 |
| Day 2 | 0.27 | 0.6047 |
| Day 3 | 1.50 | 0.2257 |
| Day 4 | 1.85 | 0.1800 |
| Day 5 | 0.82 | 0.3693 |
| Day 6 | 0.82 | 0.3683 |
| Day 7 | 0.06 | 0.8112 |
| Day 8 | 0.38 | 0.5396 |

TABLE 2-continued

| | F-Value[1] | p-Value |
|---|---|---|
| Day 9 | 0.00 | 0.9765 |
| Day 10 | 0.01 | 0.9246 |
| Day 11 | 0.03 | 0.8552 |
| Day 12 | 0.65 | 0.4228 |
| Day 13 | 0.03 | 0.8535 |
| Group 7 vs Group 1 | | |
| Day 1 | 0.50 | 0.4831 |
| Day 2 | 2.54 | 0.1167 |
| Day 3 | 3.22 | 0.0782 |
| Day 4 | 1.23 | 0.2719 |
| Day 5 | 0.40 | 0.5281 |
| Day 6 | 0.27 | 0.6030 |
| Day 7 | 0.01 | 0.9287 |
| Day 8 | 0.12 | 0.7288 |
| Day 9 | 0.03 | 0.8720 |
| Day 10 | 0.45 | 0.5048 |
| Day 11 | 0.13 | 0.7213 |
| Day 12 | 0.64 | 0.4266 |
| Day 13 | 0.03 | 0.8588 |

[1]test statistic
[2]Statistics are given from DAY 1 to 13; At DAY 0, all calculations are identical (weights set to 100%)
*statistically significant (<0.05)
**highly statistically significant (<0.0001)

3. Comparison of HΔgM-3b1-immunized animals (group 8, $10^4$ PFU/animal) with RacH-(group 2, $10^5$ PFU) and HΔgM-Ins-immunized animals (group 5, $10^4$ PFU) regarding the efficacy parameter prevention of body weight reduction after challenge. The table below presents the statistical analyses for the mouse groups that had received $10^4$ PFU per animal and reveals the following: The differences in mean body weights were statistically significantly different between animals of group 8 ($10^4$ PFU HΔgM-3b1) and that of group 5 (HΔgM-Ins) on days 1 and 11 to 13. However, in RacH-immunized animals (group 2), differences in mean body weights were significantly or highly significantly reduced on all days after infection when compared to HΔgM-3b1immunized mice (group 8).

TABLE 3

| | F-Value[1] | p-Value |
|---|---|---|
| Group 8 vs Group 5 | | |
| Day 1[2] | 6.91 | 0.0112* |
| Day 2 | 3.23 | 0.0782 |
| Day 3 | 3.08 | 0.0849 |
| Day 4 | 0.85 | 0.3614 |

TABLE 3-continued

|  | F-Value[1] | p-Value |
|---|---|---|
| Day 5 | 1.67 | 0.2014 |
| Day 6 | 0.75 | 0.3911 |
| Day 7 | 2.62 | 0.1113 |
| Day 8 | 3.23 | 0.0779 |
| Day 9 | 3.19 | 0.0800 |
| Day 10 | 4.00 | 0.0506 |
| Day 11 | 4.20 | 0.0453* |
| Day 12 | 5.75 | 0.0200* |
| Day 13 | 4.98 | 0.0299* |
| Group 8 vs Group 2 | | |
| Day 1 | 11.06 | 0.0016* |
| Day 2 | 10.75 | 0.0018* |
| Day 3 | 18.26 | 0.0001** |
| Day 4 | 14.56 | 0.0004* |
| Day 5 | 13.66 | 0.0005* |
| Day 6 | 12.44 | 0.0009* |
| Day 7 | 9.87 | 0.0028* |
| Day 8 | 11.07 | 0.0016* |
| Day 9 | 8.75 | 0.0046* |
| Day 10 | 10.08 | 0.0025* |
| Day 11 | 10.83 | 0.0018* |
| Day 12 | 10.36 | 0.0022* |
| Day 13 | 10.50 | 0.0021* |

[1]test statistic
[2]Statistics are given from DAY 1 to 13; At DAY 0, all calculations are identical (weights set to 100%)
*statistically significant (<0.05)
**highly statistically significant (<0.0001)

4. Comparison of HΔgM-3b1-immunized animals (group 9, $10^3$ PFU/animal) with RacH-(group 3, $10^3$ PFU) and HΔgM-Ins-immunized animals (group 6, $10^3$ PFU) regarding the efficacy parameter prevention of body weight reduction after challenge The table below shows the results for the lowest dose of immunization. It can be summarized that animals receiving HΔgM-3b1 at the lowest dose exhibited a (highly) significantly higher mean body weight on days 4 through 9 when compared to animals receiving the identical dose of either HΔgM-Ins or RacH. In addition, RacH-immunized animals exhibited significantly reduced body weights when compared to HΔgM-3b1-immunized animals on days 1 to 3 after challenge infection.

TABLE 4

| | F-Value[1] | p-Value |
|---|---|---|
| Group 9 vs Group 6 | | |
| Day 1[2] | 0.00 | 0.9505 |
| Day 2 | 1.55 | 0.2193 |
| Day 3 | 2.51 | 0.1190 |
| Day 4 | 22.95 | 0.0001** |
| Day 5 | 24.34 | 0.0001** |
| Day 6 | 8.23 | 0.0059* |
| Day 7 | 6.81 | 0.0118* |
| Day 8 | 4.22 | 0.0449* |
| Day 9 | 4.87 | 0.0316* |
| Day 10 | 3.60 | 0.0631 |
| Day 11 | 2.64 | 0.1103 |
| Day 12 | 3.33 | 0.0735 |
| Day 13 | 3.45 | 0.0687 |
| Group 9 vs Group 3 | | |
| Day 1 | 16.62 | 0.0002* |
| Day 2 | 15.11 | 0.0003* |
| Day 3 | 32.13 | 0.0001** |
| Day 4 | 35.92 | 0.0001** |
| Day 5 | 36.46 | 0.0001** |
| Day 6 | 23.68 | 0.0001** |
| Day 7 | 14.81 | 0.0003* |

TABLE 4-continued

| | F-Value[1] | p-Value |
|---|---|---|
| Day 8 | 9.03 | 0.0041* |
| Day 9 | 9.45 | 0.0033* |
| Day 10 | 3.77 | 0.0574 |
| Day 11 | 3.88 | 0.0542 |
| Day 12 | 3.87 | 0.0543 |
| Day 13 | 2.55 | 0.1161 |

[1]test statistic
[2]Statistics are given from DAY 1 to 13; At DAY 0, all calculations are identical (weights set to 100%)
*statistically significant (<0.05)
**highly statistically significant (<0.0001)

The present invention is not to be limited in scope by the exemplified embodiments which are intended as illustrations of single aspects of the invention. Indeed various modifications of the invention in addition to those shown and described herein will become apparent to those skilled in the art from the foregoing description and accompanying drawings. Such modifications are intended to fall within the scope of the appended claims.

All publications and patent applications cited herein are incorporated by reference in their entireties.

What is claimed is:

1. An Equine Herpes Virus strain HΔgM-3b1 deposited under accession No. 99101536 with the ECACC.

2. The Equine Herpes Virus according to claim 1 further comprising one or more heterologous genes.

3. A nucleic acid comprising a nucleotide sequence encoding the Equine Herpes Virus according to claim 1.

4. A nucleic acid comprising a nucleotide sequence encoding the Equine Herpes Virus according to claim 2.

5. A pharmaceutical composition comprising the Equine Herpes Virus according to claim 1; and a pharmaceutically acceptable carrier.

6. A method for determining whether an animal is infected with a wild type Equine Herpes Virus (EHV) or is treated with the EHV according to claim 1, comprising analyzing a nucleic acid encoding protein gM derived from the animal and comparing the nucleic acid from the animal with a nucleic acid encoding the wild type protein gM and a nucleic acid encoding the protein gM of the EHV according to claim 1.

7. A method for determining whether an animal is infected with a wild type Equine Herpes Virus (EHV) or is treated with an EHV encoded by the nucleic acid of claim 3 comprising contacting an EHV nucleic acid encoding gM derived from the animal with a nucleic acid probe capable of specifically hybridizing to a nucleic acid encoding a wild type gM protein or the nucleic acid of claim 3 and measuring the amount of any hybridization of said probe.

8. A kit comprising in one or more containers a nucleic acid probe that is capable of specifically hybridizing to a nucleic acid comprising a sequence of nucleotides encoding the nucleic acid of claim 3.

9. A pharmaceutical composition comprising the Equine Herpes Virus according to claim 2; and a pharmaceutically acceptable carrier.

10. A pharmaceutical composition comprising the nucleic acid according to claim 3; and a pharmaceutically acceptable carrier.

11. A method for improving the immune response induced by an Equine Herpes Virus (EHV) vaccine against wild type infections comprising administering the EHV according claim 1.

12. A method for improving the immune response induced by an Equine Herpes Virus (EHV) vaccine against wild type infections comprising administering the EHV according to claim 2.

13. A method for the prophylaxis or treatment of Equine Herpes Virus infection in an animal comprising administering the pharmaceutical composition according to claim 5 to said animal.

14. A method for the prophylaxis or treatment of Equine Herpes Virus infection in an animal comprising administering the pharmaceutical composition according to claim 9 to said animal.

15. A method for the prophylaxis or treatment of Equine Herpes Virus infection in an animal comprising administering the pharmaceutical composition according to claim 10 to said animal.

16. A method for determining whether an animal is infected with a wild type Equine Herpes Virus (EHV) or is treated with the EHV according to claim 1, comprising comparing an EHV protein gM derived from the animal with a wild type EHV protein gM and a protein gM of the EHV according to claim 1.

17. A method for determining whether an animal is infected with a wild type Equine Herpes Virus (EHV) or is treated with the EHV according to claim 1, comprising contacting an EHV protein gM derived from the animal with a wild type EHV protein gM or a protein gM of the EHV according to claim 1, adding an antibody that specifically binds the wild type protein gM or the protein gM of the EHV according to claim 1, and determining the binding of said antibody.

* * * * *